United States Patent [19]
Basler et al.

[11] Patent Number: 5,880,848
[45] Date of Patent: Mar. 9, 1999

[54] PROCESS AND DEVICE FOR HIGH RESOLUTION OPTICAL TESTING OF SURFACES

[75] Inventors: Norbert Basler, Hoisdorf; Jorg Fiedler, deceased, late of Ahrensburg, by Erwin Fiedler, Christel Fiedler, heirs; Bryan Hayes, Hamburg; Frank Herrmann, Bad Oldesloe, all of Germany

[73] Assignee: Basler gmbH, Ahrensburg, Germany

[21] Appl. No.: 621,116

[22] Filed: Mar. 22, 1996

[30] Foreign Application Priority Data

Mar. 27, 1995 [DE] Germany .................. 195 11 195.8

[51] Int. Cl.$^6$ ............................ G01B 11/00; G01N 21/00
[52] U.S. Cl. ............................................ 356/390; 356/237
[58] Field of Search ...................................... 356/394, 390, 356/395, 376, 237; 348/86–88, 92, 125–130

[56] References Cited

U.S. PATENT DOCUMENTS 3,740,467  6/1973  Kubo et al. .............................. 356/394
5,268,735  12/1993  Hayashi ................................. 356/237

FOREIGN PATENT DOCUMENTS

3837063 C1  3/1990  Germany .
4032327 A1  4/1992  Germany .

OTHER PUBLICATIONS

"Hohe Auflösung mit 21 Millionen Pixel", Lenz, Funkschau Teilz 1, pp. 46–47, Teil, pp. 61–63 Apr. 1989.

Reimar Lenz, "ProgRes 3000: A Digital Color Camera with a 2D Array CCD Sensor and Programmable Resolution up to 2994×2320 Picture Elements", in Medtech '89: Medical Imaging, 6–8 Nov. 1989, SPIE vol. 1357 pp. 204–209.

Primary Examiner—Frank G. Font
Assistant Examiner—Amanda Merlino
Attorney, Agent, or Firm—Howson and Howson

[57] ABSTRACT

The invention relates to a process for the optical testing of a surface of an object, particularly a compact disc, in which the surface is illuminated by at least one light source and the light reflected and/or scattered by the surface is projected onto at least one substantially flat, light-sensitive element of a light-sensitive receiver. The receiver consists of several pixels in the form of a grid in the line direction and the space direction. In a test phase at least one actual image is generated that is compared with at least one desired image which was produced in a read-in phase. To produce an image of the surface with more information the invention provides that during the read-in phase and/or the test phase at least two images of the surface are taken and the image of the surface which is projected on the light-sensitive element is displaced by at least a fraction of the dimension of a pixel in each case in at least one direction with respect to the light-sensitive element. In this way it is possible to detect the ambient field of a pixel so that the printed regions or the like can be classified for an improved evaluation, particularly when producing the desired image.

19 Claims, 3 Drawing Sheets

PROCESS AND DEVICE FOR HIGH RESOLUTION OPTICAL TESTING OF SURFACES

BACKGROUND TO THE INVENTION

The invention relates to a process for the optical testing of a surface of an object, in which the surface is illuminated by at least one light source and the light reflected and/or scattered by the surface is projected onto at least one substantially flat, light-sensitive element of a light-sensitive receiver. The receiver consists of several pixels in the form of a grid in the line direction and the space direction. In a test phase at least one actual image is generated that is compared with at least one desired image which was produced in a read-in phase. Nevertheless, the suitability of the invention for other surfaces will be recognised.

CDs have recently become increasingly popular as sound media for home use because of the high potential sound quality, and as pure data media in data processing because of the high potential data density. They are therefore a mass-market product, but have to meet high to very high quality demands, particularly when used as pure data media.

Generally speaking a CD comprises a circular disc, multi-layered in cross-section, with a central tap hole for fitting and centring in a player. From the bottom, i.e. viewed from the read side of the player, upwards the CD consists of a transparent plastic layer which contains all the data in the form of pits, a thin metal layer, generally of aluminium, for metallizing the plastic layer, and a thin lacquer layer which is usually hardened by UV light, for protecting the metal layer. The imprint, the so-called label, to provide information to the consumer, is then applied to the UV lacquer layer by means of known printing processes.

In the radial direction, in a CD several coaxial, circular regions which move outwards from the tap hole can be distinguished. Directly at the tap hole is the region used to fit the CD in the player. Adjoining this is a region in which the so-called ident code, by means of which the CD can be unequivocally identified, is impressed. There then follows the region used for the actual data storage. If the CD is recorded up to its maximum storage capacity the region ends directly on the outer edge region. Otherwise the so-called lead out or a reflective strip is arranged between the edge region of the CD and the data region.

In the manufacturing process a polycarbonate blank is initially produced by the die-casting method, wherein all data are already impressed by the die. One surface of the blank is then provided with the metallic reflective layer by the sputter process and sealed with the lacquer layer. In this process the CD is centrifuged in order to achieve a uniform distribution of the lacquer layer and as thin a layer as possible. The label is then printed on the CD.

In principle the label is of no importance to the function of the CD because a CD is read from the underside. For the consumer, however, a perfect label is often a criterion for perfect playback of the CD so that it is necessary to produce a faultless imprint on the surface of the CD. In contrast the UV lacquer layer on a CD must always be perfect because otherwise there is the risk of the underlying metal layer oxidizing prematurely, which could cause reading errors. Processes with which the surface of the CD, i.e. the label and optionally also the UV lacquer layer, can be tested are therefore required.

Generally speaking the surface of the CD is printed in any manner. Colour surfaces, pictures, inscriptions or the like can be applied with the most varied colour application processes for example. It is of course also possible for the CD to be partially unprinted, so that the metal layer is visible through the UV lacquer from the top. Furthermore a CD is often neither printed nor provided with a metal layer on the inner and outer edge region and is therefore transparent in those regions.

Generally speaking an optical process is used for testing the printed surface of the CD, in which the surface of the CD is photographed by a light-sensitive receiver in the top view from above. In a data processing unit the actual image taken is compared with a previously read-in desired image of a perfect surface with certain test criteria. Any deviation is then detected as a fault and the CD is graded according to the size and nature of the deviation.

With automatic test methods, electronic CCD cameras which convert the light received directly into electrical signals are usually used. The substantially flat light-sensitive element of a CCD camera. is constructed in the form of a grid and has a multiplicity of pixels in line and space direction. At the same time this grid is a measure of the camera's resolution. In conventional CCD cameras the light-sensitive element has approx. 750 pixels in the line direction and approx. 580 in the space direction, for example, and the resolution is approx. 0.22 mm.

It has, however, been shown that this resolution is often inadequate for testing a surface with the desired criteria. In particular, different regions require different criteria, as plane imprints must meet different criteria, for example, from regions with sharp light/dark contrasts, such as are produced by lettering. In the case of plane imprints, for example, with metallic prints there is the problem that the metallic effect is achieved by means of metal particles whose content in the imprint is irregular. With such imprints in particular it is possible for an imprint that is perfect to the human eye to be detected as a fault by the test method. With low-contrast imprints, such as solely background images, there is the risk that the boundary lines will not be detected perfectly so that potential faults cannot be identified.

Particularly where electronic CCD cameras are used there is a further problem in that a pixel actually has only a limited photo-sensitive region which is surrounded by a region that is not photo-sensitive. Tracks are then arranged in this region for example. This means that the surface is not photographed in its entirety and the immediate ambient field of an exposed pixel not detected at all.

In principle it is of course possible to improve the test by increasing the resolution of the camera used. Increasing the resolution is not, however, possible without expense. Furthermore the fact that the light-sensitive element would have substantially more pixels, thereby prolonging the computing time required to test the surface, is a disadvantage. In addition the light-sensitive receiver will then be larger in size and can no longer be readily incorporated in the test device which often needs to have a limited structural volume because it is incorporated into existing production plants.

SUMMARY OF THE INVENTION

The object of the invention is therefore to improve a process of the above-mentioned kind in such a way that an image of the surface with substantially more data can be produced with an unchanged resolution of the light-sensitive receiver.

According to the invention the object is achieved in that during the read-in phase and/or the test phase at least two images of the surface are taken and the image of the surface which is projected on the light-sensitive element is displaced by at least a fraction of the dimension of a pixel in at least one direction with respect to the light-sensitive element. This measure means that in addition to the image that was taken in the rest or initial position, at least one further image is produced in which the pixels of the light-sensitive element record a part of the picture element originally recorded and a part of the picture element which was originally adjacent. The ambient field of every individual picture element can be advantageously detected in this way. In addition it is possible to classify the region of the CD and/or the type of the imprint by comparison with the other images produced on the basis of this relative displacement. A further advantage is that the regions of the surface which had previously been projected on regions of the light-sensitive element in which the non-photo-sensitive regions of a pixel are arranged can now also be detected.

When reading-in a perfect CD, for example., it can be assumed that an entire region has a light or dark, substantially monochrome imprint if the pixel is exposed light or dark both in the rest position and after the relative displacement, for example. If, for example, two adjacent pixels are grey in the rest position and at least one pixel dark or light after the relative displacement, then sharp light/dark contrasts are present. In any event, with the process according to the invention additional information is obtained which can be processed during the read-in phase to produce a desired image, for example.

An embodiment of the invention provides that a relative displacement by the dimensions of half a pixel takes place. Appropriately provision can be made for four images to be recorded during the test phase and/or the read-in phase, wherein, starting from a rest position, the projected image is displaced with respect to the light-sensitive element by a fraction of the dimension of a pixel in each case, in the line direction, in the space direction and in line and space direction of the grid of the light-sensitive element. This has the advantage that the entire ambient field of a pixel can be detected. In principle, eight displacements and hence eight additional images would be required to detect the entire ambient field of an open pixel, starting from the rest position. In the case of a displacement by the dimension of half a pixel, however, five regions of the ambient field, which would have to be recorded by means of five additional images, are recorded by the displaced adjacent pixels, so that the production of three additional images is sufficient.

In a possible embodiment of the invention provision can be made for the surface of the object to be moved with respect to the light-sensitive element. If the object, such as the CD, is moved, the actuating means would have to cooperate with the mounting of the object or directly with the object. It is, however, only possible to make such a slight lateral movement of the object, which would be required for the relative displacement, with complicated actuating elements and by correspondingly locating the mounting device inside the device. The same substantially applies if the light-sensitive receiver is moved. Furthermore the light-sensitive receiver has sensitive optics which could be disturbed by the continuous movements.

A particularly advantageous embodiment of the invention therefore provides that before impacting on the light-sensitive element the light reflected and/or scattered by the surface is reflected on at least one mirror element which is pivoted about at least one axis in order to bring about the relative displacement of the projected image with respect to the light-sensitive element. This has the advantage that both the light-sensitive receiver and the object maintain fixed positions whereas only an optical intermediate element is moved. In particular it is an advantage that the mirror only needs to be pivoted, which is possible with high accuracy with relatively simple means. Furthermore there is no risk of the optics being changed in the course of time.

An appropriate embodiment provides that the mirror element is pivoted by means of at least one piezoelectric element. Advantageously such elements permit a small movement with high accuracy and reproducibility. In addition, piezoelectric elements can easily be controlled in a quick and troublefree manner by electronic pulses from a data processing unit, for example, so that it is quite straightforward to automate the read-in process to produce the desired image and/or record several images during the test phase.

Provision can also be made for the light rays reflected and/or scattered by the surface to be concentrated on the objective of the light-sensitive receiver by at least one lens arrangement. It can be appropriate for the light rays concentrated by the lens arrangement to be moved with respect to the light-sensitive receiver. In this case it is particularly appropriate when the concentrated light rays are moved by the mirror element with respect to the light-sensitive receiver. This has the advantage that the mirror for deflecting the light rays onto the light-sensitive receiver and for achieving the relative displacement can have relatively small dimensions. This can prevent problems when moving the mirror such as would be caused by too high a moment of inertia or too heavy a weight.

The invention also relates to a device for the optical testing of a surface of an object, particularly a compact disc (CD), in which the surface can be illuminated by at least one light source and the light reflected and/or scattered by the surface is projected onto at least one substantially flat light-sensitive element of a light-sensitive receiver which consists of several pixels in the form of a grid in the line direction and in the space direction. To implement the process according to the invention in particular it is provided that setting means are present in order to displace the projected image of the surface in at least one direction by at least a fraction of the dimension of a pixel with respect to the light-sensitive element. The ambient field of the picture element originally recorded can be detected by means of the relative displacement of the projected image by, for example, the dimension of half a pixel. With the additional information different regions, different imprints or the like can be classified, when the desired image is produced for example.

A possible embodiment provides that the setting means are connected to the light-sensitive element and/or the object in order to bring about the relative displacement. It is, however, particularly appropriate if at least one mirror element is arranged between the light-sensitive receiver and the surface on which the light is at least partially reflected before impacting on the light-sensitive element, and the mirror element can be pivoted about at least one axis by the setting means, in order to bring about the relative displacement. This has the advantage that the setting means can be relatively simple in form as an optical element with relatively low weight has to be pivoted. It is also an advantage that a relatively insensitive optical element is moved so that the danger of the optics being undesirably disturbed by the movement is prevented.

It can be appropriate for the setting means to have at least one piezoelectric element. Such piezoelectric elements have the advantage of being able to carry out small movements with high accuracy. Furthermore they are simple to control by means of electrical signals which can be generated with a data processing unit for example.

Provision can be made for the piezoelectric element to be fixed to the back of the mirror element. It can also be appropriate for the piezoelectric element to have at least three rams that operate piezoelectrically and act on the mirror element in such a way that a pivot about a first axis parallel to the mirror surface, about a second axis parallel to the surface and perpendicular to the first axis as well as a simultaneous pivot about both axes can be brought about. By means of such a pivot about one or two axes the projected image is displaced with respect to the light-sensitive element and the entire ambient field of the picture element originally recorded, i.e. the pixel originally exposed, can be detected. Particularly in the case of a relative displacement by the dimension of half a pixel the entire ambient field can be detected by means of three additional images since a part of the ambient field is recorded by the adjacent pixels after the above-mentioned displacements.

It can be appropriate for the mirror element to be retained on the piezoelectric element in the rest position by means of a spring. This has the advantage that the entire optics have a fixed rest position which is only changed by actuating the piezoelectric elements. This is particularly advantageous if a relative displacement of the projected image should only take place during the read-in phase because there is insufficient time during the test phase, for example, to produce several images. The mirror then remains in its rest position during the test phase.

An advantageous embodiment provides that at least one lens arrangement is provided between the light-sensitive receiver and the surface in order to concentrate the rays reflected and/or scattered by the surface before they enter the objective of the light-sensitive receiver. It is appropriate in this case if the mirror element which can be pivoted by the setting means is arranged between the lens arrangement and the light-sensitive receiver. This has the advantage that the pivotable mirror can have relatively small dimensions so that problems when operating, which might arise because of a heavy weight or a high moment of inertia, for example, are avoided.

BRIEF DESCRIPTION OF THE DRAWINGS

The invention will be described in greater detail below by way of example and with the aid of the accompanying diagrammatic drawing in which.

DESCRIPTION OF THE PREFERRED EMBODIMENTS

Figure 1:
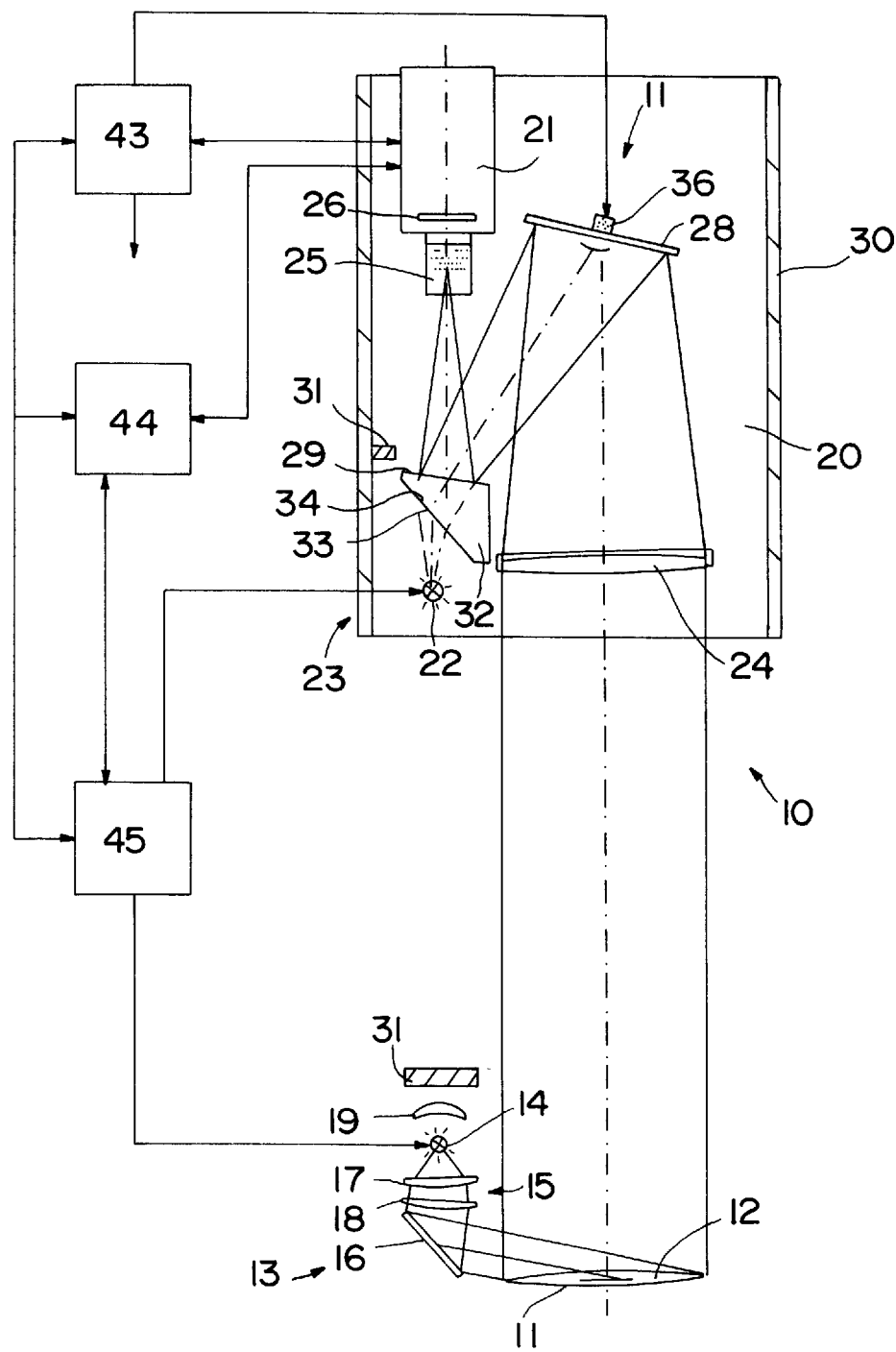
FIG. 1 shows a device according to the invention.
Figure 2:
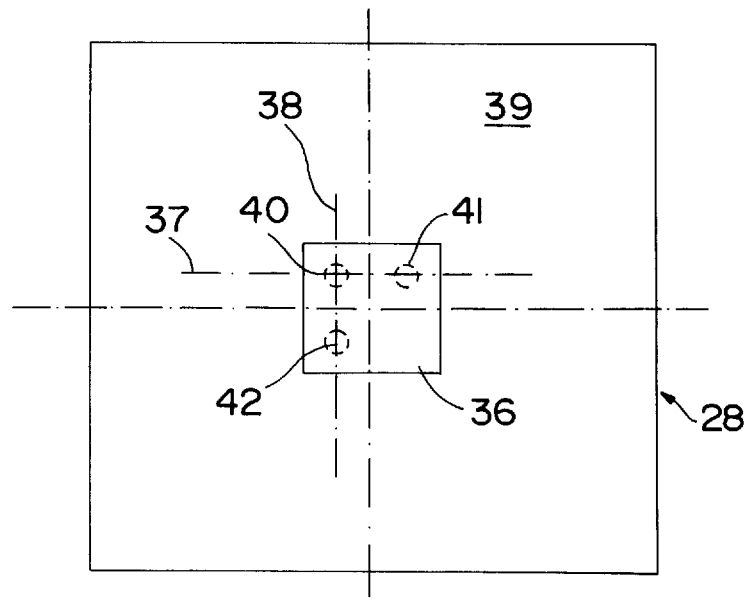
FIG. 2 shows a view of the pivotable mirror in the direction of the arrow II in FIG. 1 and FIGS. 3a–3c each show a grid of the surface under test of an object.

The device 10 for the optical testing of a surface of a compact disc (CD) which is shown in FIG. 1 has a generally columnar vertical structure to which the individual functional elements are secured. For reasons of clarity the retaining devices required to secure the individual functional elements are not shown in the drawing.

In its lower section the device 10 has a mounting device, which is also not shown, for receiving and centering a CD 11 for the test. From the side the surface 12 of the CD 11 can be illuminated with light with a sharp angle of incidence by means of a lower light 13. More specifically the arrangement is such that the lower light 13 is only arranged on one side of the CD. The lower light has a light source 14, the light rays from which are directed onto the surface 12 of the CD 11 through a lens arrangement 15 and a mirror 16. In the direction of the irradiation from the light source 14 a round convergent lens 17 and a cylindrical lens 18 are arranged in order to illuminate the surface 12 with a pencil of rays which has slightly convergent rays viewed from above and substantially parallel rays viewed from the side. The cylindrical lens 18 is tiltably mounted about a longitudinal axis perpendicular to the drawing plane. This means that the cylindrical lens 18 can be aligned in such a way that the entire surface can be illuminated with substantially identical light intensity by utilizing the lens errors. A concave mirror 19 can also be provided behind the light source 14 to increase the luminous efficacy.

Above the CD 11 a superstructure 20 of the test device 10 is provided in which a light-sensitive receiver 21 for photographing the surface 12 of the CD 11 in the top view, a light source 22 for an upper light 23 and a lens arrangement 24 for aligning the light rays onto the surface 12 and for concentrating the reflected and/or scattered light coming from the surface 12 into the objective 25 of the light-sensitive receiver 21 are arranged. By means of the lens arrangement 24, an achromatic lens for example, the light emitted from the upper light 23 is aligned parallel onto the surface 12 and at the same time the light coming from the surface 12 is projected into the objective 25 of the light-sensitive receiver 21. The width of the device 10 perpendicular to the drawing plane can be reduced because of the substantially parallel beam path between the lens arrangement 24 and the surface 12 of the CD 11.

Behind its objective 25 the light-sensitive receiver 21 has a substantially flat light-sensitive element 26 which has a multiplicity of pixels 27. The pixels 27 are arranged in the line direction (X direction) and space direction (Y direction) to form a grid.

In the direction in which the light radiates from the surface 12 the light is deflected twice, through a first plane mirror element 28 and through a second plane mirror surface 29, before it enters the objective 25 of the light-sensitive receiver. This beam deflection enables the structural height to be reduced. This is appropriate because the focal length, of an achromatic lens for example, cannot be arbitrarily small, so that the device would be relatively tall without the beam deflection.

The superstructure 20 is surrounded by a sleeve-like cover element 30 to prevent the ambient area from being dazzled by the upper light 23 and the light-sensitive receiver 21 from being influenced by ambient light. This sleeve-like cover element 30 can have a rectangular cross-section, the inner width of which at least corresponds to the external diameter of the lens arrangement 24. Corresponding cover elements 31 can be provided between the light source 22 for the upper light 23 and the objective of the light-sensitive receiver 21 to prevent direct exposure. Such cover elements 31 are also provided at corresponding points for the light source 14 for the lower light 13. Provision can also be made for the light sources to be provided with corresponding cover means which are not shown in order to emit light in a preferred direction only.

By means of the parallel beam path between the lens arrangement 24 and the surface 12 of the CD 11 in the form of a telecentric structure it is possible to vary the distance between the superstructure 20 and the surface of the object without changing the optics in the superstructure. Corresponding guide rails on which the superstructure 20 can be movably mounted can be provided for this purpose. These structural elements are not shown for reasons of clarity.

In the device 10 shown, the upper light 23 is brought towards the lens arrangement 24 by means of an optical prism 32. The prism 32 means that the lens arrangement 24 can fix rays on two focal points. This is required because on the one hand, the light source 22 for the upper light must be in a focal point of the lens arrangement 24 for optimum illumination by the upper light. On the other hand the objective 25 of the light-sensitive receiver 21 must be in a focal point of the lens arrangement 24 for a sharp image of the surface 12. The use of a prism means that two focal points of the lens arrangement are generated and that the focal points have no direct optical connection, i.e. that a light beam from the light source 22 can only reach the light-sensitive receiver 21 via the surface 12 of the CD 11.

More specifically the arrangement is such that the optical prism 32 has a semi-reflecting mirror surface which forms the mirror surface 29. The prism 32 also has a second lateral surface 33; the light source 22 for the upper light is arranged on its side facing away from the semi-reflecting mirror surface. This second lateral surface 33 runs at an angle α to the semi-reflecting mirror surface 29 such that the light rays emanating from the light source 22 run precisely opposite to the light rays coming from the surface, through refraction at the second lateral surface and through further refraction at the semi-reflecting mirror surface. In this case the light source 22 is arranged in the second focal point of the lens arrangement 24 produced by the prism 32 acting as beam splitting means.

Furthermore the angle α is selected in such a way that the light-sensitive receiver 21 cannot see directly into the light source 22. This means that light rays which would emanate from the light-sensitive receiver 21 experience total reflection at the inner boundary surface 34 of the second lateral surface 33. These rays then impinge on a third side 35 of the prism which is blackened for example. Blackening this side also has the advantage that any influence from diffused light can be avoided. By a corresponding setting of the angle α between the lateral surfaces 29 and 33, therefore, a direct illumination of the light-sensitive receiver by the light source 22 for the upper light can be prevented.

The angle α should be selected according to the local circumstances, i.e. particularly the position of the prism in the beam path and the material used for the prism. The person skilled in the art will know how to determine the angle in order to meet the requirements and so there is no need for further explanation of it.

The first mirror element 28 is provided with a setting element which is in the form of a piezoelectric element 36 for example. Corresponding actuation of the setting element makes it possible for the mirror 28 to be pivoted about its axes 37 and/or 38 which run in the mirror plane, so as to displace the projected image with respect to the light-sensitive element 26. More specifically the arrangement is such that the piezoelectric element 36 is arranged on the back 39 of the mirror, wherein the mirror 28 is retained within the superstructure 20 by the piezoelectric element 36 at the same time. A disc spring which holds the mirror 28 in a rest position and is not shown in the drawing is provided for this purpose. Three rams 40, 41 and 42 are provided to pivot the mirror out of its rest position, so as to pivot the mirror about the axes 37 and/or 38 by corresponding actuation.

The stroke of the rams (40, 41, 42) is dimensioned in such a way that the pivoting of the mirror 28 about the corresponding axis causes the projected image to be displaced by the dimension of half a pixel in each case. Depending on the alignment of the mirror, a pivot about the axis 37 can cause a displacement in the X direction (FIG. 3a), a pivot about the axis 38 a displacement in the Y direction (FIG. 3b) and a pivot about both axes a displacement in the X and Y direction (FIG. 3c).

Figure 3A:
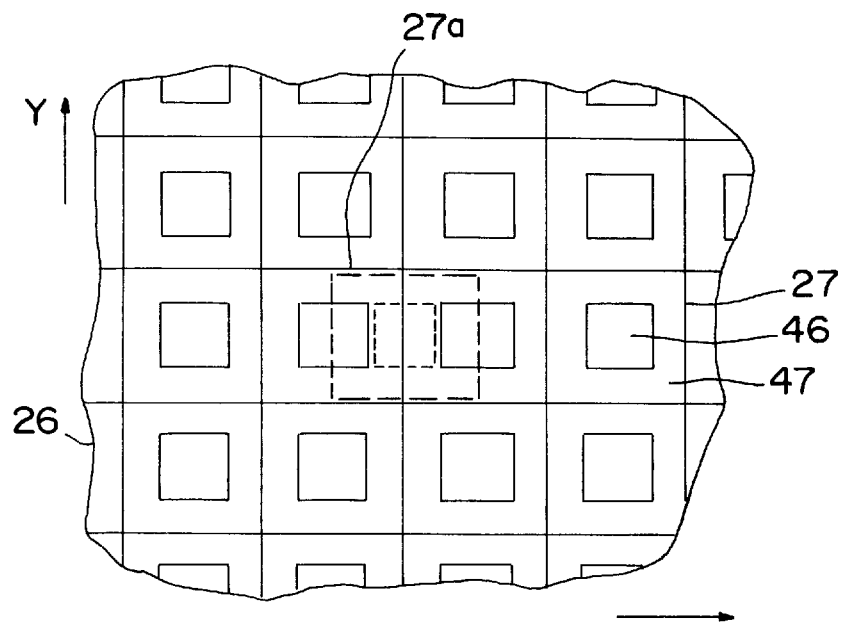
Figure 3B:
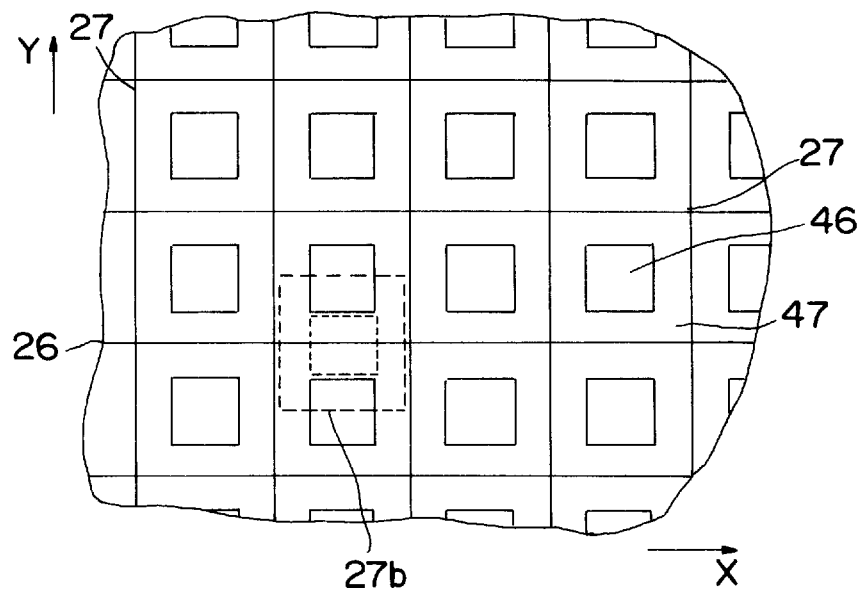
Figure 3C:
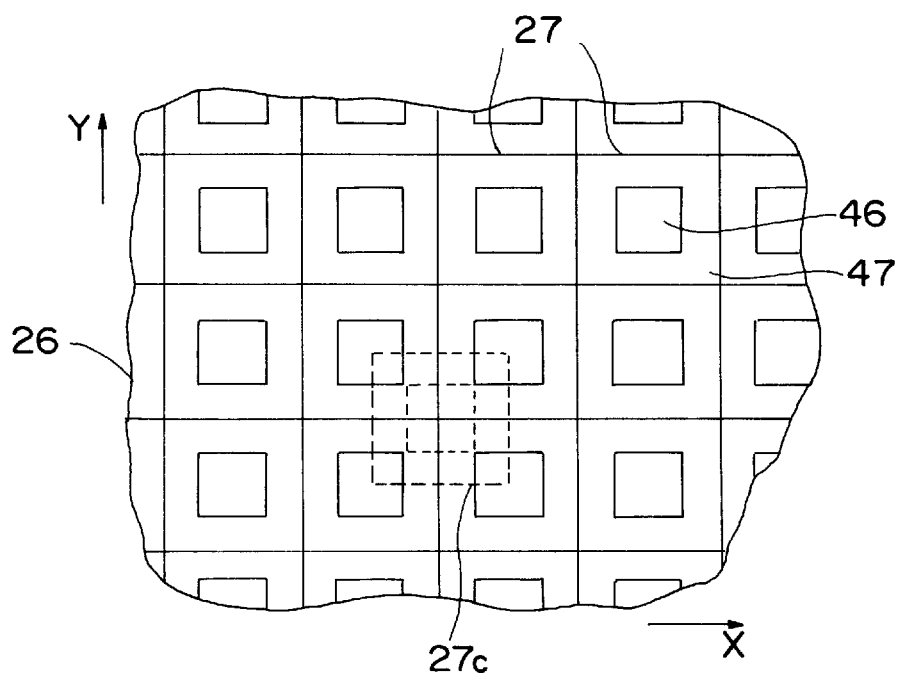

As can be seen from FIGS. 3a to 3c in particular, by means of this relative displacement the ambient field of a pixel 27 can be scanned without the need to increase the resolution of the light-sensitive receiver. In the drawing the grid of the light-sensitive element 26 is shown in the initial position with solid lines. As shown in the illustrations, a pixel 27 has a photo-sensitive region 46 which is surrounded by a non-photo-sensitive region 47. Exposure in the rest position only would therefore produce an only incomplete image of the surface.

By means of the displacement in the X direction, the dashed region 27a shown in FIG. 3a is photographed by the pixel exposed in the initial position; half of it comprises the picture element originally photographed and the other half the adjacent picture element. The same applies to the displacement in the Y direction (dashed region 27b in FIG. 3b) and in the X and Y direction (dashed region 27c in FIG. 3c). In the case of a displacement in both directions the region comprises part of the picture element photographed in the initial position, parts of the two adjacent picture elements and part of a picture element which adjoins at a corner. The other edge regions coincide with the exposures of the adjacent pixels which were obtained by means of the displacements. In this way the entire ambient field of a pixel can be scanned. With a relative displacement by half a pixel, therefore, only four images, i.e. three additional images starting from the initial position, are required. In the embodiment shown in particular the photo-sensitive region 4G of the pixel is displaced into the previously non-photo-sensitive region 47 of two adjacent pixels.

In principle the resolution can be increased by means of a displacement smaller than half a pixel. In this case, however, more photographs are required to detect the ambient field; these require more time which is often not available in a continuous test process.

The light-sensitive receiver 21 is connected to a data processing unit 43 which compares the actual images taken with at least one desired image that has already been read-in. The data processing unit 43 is also connected to the piezoelectric element 36 to control the relative displacements and synchronize the light-sensitive receiver and optionally the lighting with the displacements.

Furthermore, a first and a second control means 44 and 45 are provided to adjust the exposure time of the light-sensitive receiver 21 and/or the illumination of the surface by the upper light 23 and/or the lower light 13. The first control means is connected to the second control means in order to permit synchronization between the lighting and the light-sensitive receiver.

Provision can, for example, be made for two images of the surface to be taken within one test period in order to prevent a contrast weakening in the images in question, which could take place if there was simultaneous illumination from the upper light and the lower light. Provision can be made for the upper light to take the form of a flashlight whereas the lower light is a constant light. During the flash the light-sensitive receiver, usually a CCD camera, is switched into the so-called shutter mode so as to set the correspondingly short exposure time. The flashlight causes a substantially stronger exposure of the camera so that the simultaneous exposure with the continuous lower light is barely effective in the photograph taken. Two images of a surface can thus be produced simply and in a very short time indeed.

The drawing and the description have not described the individual angles to be maintained in greater detail because they depend in particular on the different dimensions of the various elements. The person skilled in the art will be able to determine and set the precise alignments of the elements in question with the aid of the description, without needing further explanation.

List of reference numerals:
10 Device
11 CD non-photo-sensitive region
12 Axis
13 Lower light
14 Light source
15 Lens arrangement
16 Mirror
17 Lens
18 Cylindrical lens
19 Concave mirror
20 Superstructure
21 Light-sensitive receiver
22 Light source
23 Upper light
24 Lens arrangement
25 Objective
26 Light-sensitive element
27 Pixel (picture element)
28 Mirror
29 Mirror surface
30 Cover element
31 Cover element
32 Prism
33 Side
34 Boundary surface
36 Piezoelement
37 Axis
38 Axis
39 Back
40 Ram
41 Ram
42 Ram
43 Data processing unit
44 First control means
45 Second control means
46 Photo-sensitive region
47 Non-photo-sensitive region It is claimed:

1. A process for the optical testing of a surface of an object, in which the surface is illuminated by at least one light source and the light reflected and scattered by the surface is projected onto at least one substantially flat, light-sensitive element of a light-sensitive receiver which consists of several pixels in the form of a grid in the line direction and the space direction, wherein in a test phase at least one actual image is generated that is compared with at least one desired image which was produced in a read-in phase, and during the read-in phase and the test phase at least two images of the surface are taken and the image of the surface which is projected on the light-sensitive element is displaced by at least a fraction of the dimension of a pixel in at least one direction with respect to the light-sensitive element, wherein both the light-sensitive element and the surface remain in a fixed stationary position during the read-in phase and the test phase, and wherein before impacting on the light-sensitive element the light reflected and scattered by the surface is reflected on at least one mirror element which is pivotable about at least one axis in order to bring about the relative displacement of the projected image with respect to the light-sensitive element.

2. A process according to claim 1 wherein a relative displacement by the dimension of half a pixel takes place.

3. A process according to claim 2, wherein four images are recorded during the test phase and the read-in phase, wherein, starting from a rest position, the projected image is displaced with respect to the light-sensitive element in the line direction, in the space direction and in the line and space direction of the grid of the light-sensitive element.

4. A process according to claim 1, wherein four images are recorded during the test phase and the read-in phase, wherein, starting from a rest position, the projected image is displaced with respect to the light-sensitive element by a fraction of the dimension of a pixel in each case, in the line direction, in the space direction and in line and space direction of the grid of the light-sensitive element.

5. A process according to claim 1 wherein the mirror element is pivoted by means of at least one piezoelectric element.

6. A process according to claim 1 wherein the light rays reflected and scattered by the surface are concentrated on the objective of the light-sensitive receiver by at least one lens arrangement.

7. A process according to claim 6 wherein the light rays concentrated by the lens arrangement are moved with respect to the light-sensitive receiver.

8. A process according to claim 7 wherein the concentrated light rays are moved by the mirror element with respect to the light-sensitive receiver.

9. A device for the optical testing of a surface of an object, particularly a compact disc, in which the surface can be illuminated by at least one light source and the light reflected and scattered by the surface is projected onto at least one substantially flat light-sensitive element of a light-sensitive receiver which consists of several pixels in the form of a grid in the line direction and in the space direction, comprising setting means for displacing the projected image of the surface in at least one direction by at least a fraction of the dimension of a pixel with respect to the light-sensitive element, wherein at least one mirror element is arranged between the light-sensitive receiver and the surface on which the light is at least partially reflected before impacting on the light-sensitive element, wherein both the light-sensitive element and the surface remain in a fixed stationary position during the optical testing, and wherein the mirror element is pivotable about at least one axis by the setting means, in order to bring about the relative displacement.

10. A device according to claim 9 wherein the setting means has at least one piezoelectric element.

11. A device according to claim 10 wherein the piezoelectric element is fixed to the back of the mirror element.

12. A device according to claim 11 wherein the piezoelectric element has at least three rams which act on the mirror element in such a way that a pivot about a first axis parallel to the mirror surface, about a second axis parallel to the surface and perpendicular to the first axis as well as a simultaneous pivot about both axes can be brought about.

13. A device according to claim 12 wherein the mirror element is retained on the piezoelectric element in the rest position by means of a spring.

14. A device according to claim 9 wherein at least one lens arrangement is provided between the light-sensitive receiver and the surface in order to concentrate the rays reflected and scattered by the surface before they enter the objective of the light-sensitive receiver.

15. A device according to claim 14 wherein the mirror element which can be pivoted by the setting means is arranged between the lens arrangement and the light-sensitive receiver.

16. A process for optically testing a printed surface of a compact disc, comprising the steps of:

positioning a perfect compact disc having a perfect printed surface during a read-in phase in a stationary fixed position relative to at least one substantially flat, light-sensitive element of a fixed stationary light-sensitive receiver which consists of a plurality of pixels in the form of a grid in a line direction and a space direction;

illuminating said perfect printed surface of said perfect compact disc during said read-in phase with at least one light source;

projecting the light reflected and scattered by said perfect printed surface during said read-in phase onto at least one mirror element which is pivotable about at least one axis;

projecting the light reflected by said at least one mirror element during said read-in phase onto said light-sensitive element for generating an original desired image of said perfect printed surface;

pivoting said at least one mirror element during said read-in phase after generating said original desired image to bring about a relative optical displacement of said stationary perfect compact disc by a fraction of the dimension of a pixel in at least one direction with respect to said stationary light-sensitive element;

enhancing the resolution of said original desired image during said read-in phase after said at least one mirror element is pivoted by recording with said light-sensitive element and combining with said original desired image a second image of said perfect printed surface thereby creating an enhanced desired image;

positioning, during a test phase, a compact disc having a printed surface to be tested in a stationary fixed position relative to at least one substantially flat, light-sensitive element of a fixed stationary light-sensitive receiver which consists of a plurality of pixels in the form of a grid in a line direction and a space direction;

illuminating said printed surface to be tested during said test phase with at least one light source;

projecting the light reflected and scattered by said printed surface to be tested during said test phase onto at least one mirror element which is pivotable about at least one axis;

projecting the light reflected by said at least one mirror element during said test phase onto said light-sensitive element for generating an original actual image of said printed surface to be tested;

pivoting said at least one mirror element during said test phase after generating said original actual image to bring about a relative optical displacement of said stationary compact disc to be tested by a fraction of the dimension of a pixel in at least one direction with respect to said stationary light-sensitive element;

enhancing the resolution of said original actual image during said test phase after said at least one mirror element is pivoted by recording with said light sensitive element and combining with said original actual image a second image of said printed surface to be tested thereby creating an enhanced actual image; and comparing said enhanced actual image with said enhanced desired image.

17. A process according to claim 16, wherein during said recording of said original desired image each of said pixels generates a recording of a photo-sensitive region and a surrounding non-photo-sensitive region; and wherein during said recording of said second desired image each of said pixels generates a recording of a part of said photo-sensitive region of said original desired image and a part of said non-photo-sensitive region of said original desired image; whereby said enhanced desired image provides improved detection capability of light-to-dark contrasts within each pixel.

18. A process according to claim 17, wherein during said recording of said original actual image each of said pixels generates a recording of a photo-sensitive region and a surrounding non-photo sensitive region; and wherein during said recording of said second actual image each of said pixels generates a recording of a part of said photo sensitive region of said original actual image and a part of said non-photo sensitive region of said original actual image; whereby said enhanced actual image provides improved detection capability of light-to-dark contrasts within each pixel.

19. A process according to claim 18, wherein said process is automated and continuous.

* * * * *